(12) United States Patent
Suzuki

(10) Patent No.: US 6,882,927 B2
(45) Date of Patent: Apr. 19, 2005

(54) FAILURE DIAGNOSTIC APPARATUS AND FAILURE DIAGNOSTIC METHOD FOR GAS CONCENTRATION DETECTING APPARATUS

(75) Inventor: Yusuke Suzuki, Susono (JP)

(73) Assignee: Toyota Jidosha Kabushiki Kaisha, Toyota (JP)

(*) Notice: Subject to any disclaimer, the term of this patent is extended or adjusted under 35 U.S.C. 154(b) by 0 days.

(21) Appl. No.: 10/734,144

(22) Filed: Dec. 15, 2003

(65) Prior Publication Data

US 2004/0134777 A1 Jul. 15, 2004

(30) Foreign Application Priority Data

Jan. 9, 2003 (JP) ........................................ 2003-003690

(51) Int. Cl.[7] ........................... G01N 27/26; F02D 41/22
(52) U.S. Cl. ....................... 701/109; 73/23.31; 204/401; 204/424
(58) Field of Search ................................. 701/109, 114, 701/115; 73/23.31, 23.32; 204/401, 424, 425, 426

(56) References Cited

U.S. PATENT DOCUMENTS

| | | | |
|---|---|---|---|
| 4,951,632 A | 8/1990 | Yakuwa et al. | ............. 123/688 |
| 6,301,951 B1 * | 10/2001 | Lenfers et al. | ............. 73/23.31 |
| 6,547,955 B1 * | 4/2003 | Hada et al. | ................. 204/424 |
| 2002/0050455 A1 | 5/2002 | Kurokawa et al. | .......... 204/431 |

FOREIGN PATENT DOCUMENTS

| | | |
|---|---|---|
| EP | A1-0-887-640 | 12/1998 |
| EP | A2-1-202-048 | 5/2002 |
| JP | A-58-027838 | 2/1983 |
| JP | U 58-154459 | 10/1983 |

* cited by examiner

*Primary Examiner*—Hieu T. Vo
(74) *Attorney, Agent, or Firm*—Oliff & Berridge, PLC (57) ABSTRACT

A failure diagnostic apparatus for a gas concentration detecting apparatus is provided, which can early detect disconnection in a cell included in the gas concentration detecting apparatus. The gas concentration detecting apparatus is provided, which includes cells each of which pumps out oxygen in a gas detection chamber, thereby generating an electric current corresponding to the concentration of oxygen in the gas detection chamber. A heater which heats each of the cells to an activation temperature is provided. A period during which a predetermined electric current should flow in the cell after the heater starts heating is detected. A determination on whether there is disconnection is made based on whether each of electric currents flowing in the cells is appropriate.

16 Claims, 6 Drawing Sheets

\* FIGS SHOW OUTPUT BEHAVIOR WHEN A/F OF EXHAUST GAS IS LEAN

FIG. 3C

ELECTRIC CURRENT IS OUTPUT DUE TO OXYGEN WHICH REMAINS AROUND MONITOR CELL OR SENSOR CELL, OR OXYGEN WHICH HAS BEEN ADSORBED BY ELECTRODE
→ IF THERE IS NO OUTPUT, THERE IS DISCONNECTION

FIG. 3D

ELAPSED TIME AFTER WARMING-UP IS STARTED

FAILURE DIAGNOSTIC APPARATUS AND FAILURE DIAGNOSTIC METHOD FOR GAS CONCENTRATION DETECTING APPARATUS

INCORPORATION BY REFERENCE

The disclosure of Japanese Patent Application No. 2003-003690 filed on Jan. 9, 2003, including the specification, drawings and abstract is incorporated herein by reference in its entirety.

BACKGROUND OF THE INVENTION

1. Field of the Invention

The invention relates to a failure diagnostic apparatus and a failure diagnostic method for a gas concentration detecting apparatus. More particularly, the invention relates to a failure diagnostic apparatus and a failure diagnostic method which are suitable for detecting disconnection in a gas concentration detecting apparatus which detects the concentration of NOx contained in exhaust gas from an internal combustion engine.

2. Description of the Related Art

As a gas concentration detecting apparatus which detects the concentration of NOx contained in exhaust gas from an internal combustion engine, for example, an apparatus according to related art disclosed in Japanese Patent Laid-Open Publication No. 2002-202285 is known. The apparatus according to related art includes a pump cell which discharges oxygen from exhaust gas flowing into a gas detection chamber, and a monitor cell and a sensor cell which are disposed downstream of the pump cell.

The monitor cell discharges oxygen which remains in the gas detection chamber after the pump cell discharges oxygen, thereby generating an electric current corresponding to the concentration of oxygen. Meanwhile, the censor cell decomposes NOx contained in the exhaust gas into nitrogen and oxygen after the pump cell discharges oxygen, and discharges the resultant oxygen and the oxygen that remains in the exhaust gas, thereby generating an electric current.

According to the aforementioned configuration, the value of the electric current flowing in the monitor cell corresponds to the concentration of the oxygen which cannot be discharged by the pump cell. Also, the value of the electric current flowing in the sensor cell corresponds to the sum of the concentration of the oxygen which cannot be discharged by the pump cell and the concentration of the oxygen generated by decomposition of NOx. Therefore, by subtracting the value of the electric current flowing in the monitor cell from the value of the electric current flowing in the sensor cell, it is possible to detect the concentration of oxygen generated as a result of decomposition of NOx. The concentration of the oxygen thus detected corresponds to the concentration of NOx that exists in the exhaust gas. Accordingly, the aforementioned gas concentration detecting apparatus according to related art can accurately detect the concentration of NOx in the exhaust gas.

The aforementioned gas concentration detecting apparatus according to related art is used for emission control of an internal combustion engine, or the like. When output of the gas concentration detecting apparatus is used for emission control or the like, it is desirable to early detect abnormality of the gas concentration detecting apparatus in order to maintain a desired emission characteristics. However, a method for early detecting disconnection in the gas concentration detecting apparatus of this type has not been established.

SUMMARY OF THE INVENTION

In view of the above, it is an object of the invention to provide a failure diagnostic apparatus and a failure diagnostic method which can early detect disconnection in a cell included in a gas concentration detecting apparatus.

In order to achieve the aforementioned object, an aspect of the invention relates to a failure diagnostic apparatus and a failure diagnostic method for a gas concentration detecting apparatus. The failure diagnostic apparatus includes a heater which heats, to an activation temperature, a cell of the gas concentration detecting apparatus which pumps out oxygen in subject gas, thereby generating an electric current corresponding to a concentration of oxygen in the subject gas; a flowing period detector which detects a period during which a predetermined electric current should flow in the cell after the heater starts heating; and a determining device which determines there is disconnection in the cell when the electric current flowing in the cell is smaller than the predetermined electric current during the period in which the predetermined electric current should flow in the cell.

The failure diagnostic method includes the steps of heating, to an activation temperature, a cell of a gas concentration detecting apparatus which pumps out oxygen in subject gas, thereby generating an electric current corresponding to a concentration of oxygen in the subject gas; detecting a period during which a predetermined electric current should flow in the cell after heating of the cell is started; and determining there is disconnection in the cell when the electric current flowing in the cell is smaller than the predetermined electric current during the period in which the predetermined electric current should flow in the cell.

According to the aforementioned failure diagnostic apparatus and the failure diagnostic method, whether there is disconnection in the cell can be determined based on whether the predetermined electric current flows in the cell after the heating of the cell is started.

BRIEF DESCRIPTION OF THE DRAWINGS

The above mentioned embodiment and other embodiments, objects, features, advantages, technical and industrial significance of this invention will be better understood by reading the following detailed description of the exemplary embodiments of the invention, when considered in connection with the accompanying drawings, in which.

DETAILED DESCRIPTION OF THE PREFERRED EMBODIMENTS

In the following description, the present invention will be described in more detail in terms of exemplary embodiments.

Like components will be designated by like reference characters and repetitive descriptions thereof shall be omitted.

Figure 1:
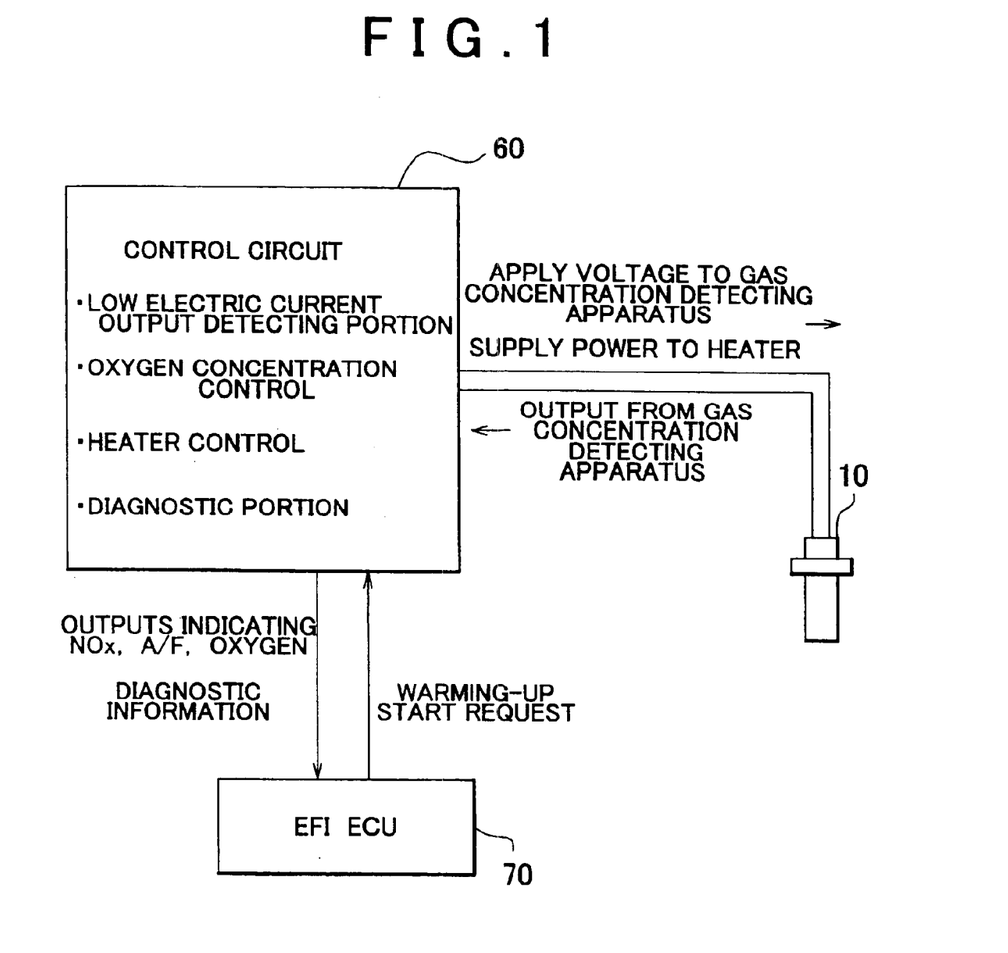
FIG. 1 is a conceptual diagram describing the configuration of a gas concentration detecting apparatus and a failure diagnostic apparatus according to an embodiment of the invention.

FIG. 1 is a conceptual diagram describing the configuration of a gas concentration detecting apparatus and a failure diagnostic apparatus according to an embodiment of the invention. A gas concentration detecting apparatus 10 shown in FIG. 1 is disposed in an exhaust passage of an internal combustion engine, particularly in an exhaust passage provided with a NOx storage catalyst. The gas concentration detecting apparatus 10 is a sensor which generates a sensor output corresponding to the concentration of NOx in exhaust gas.

Figure 2:
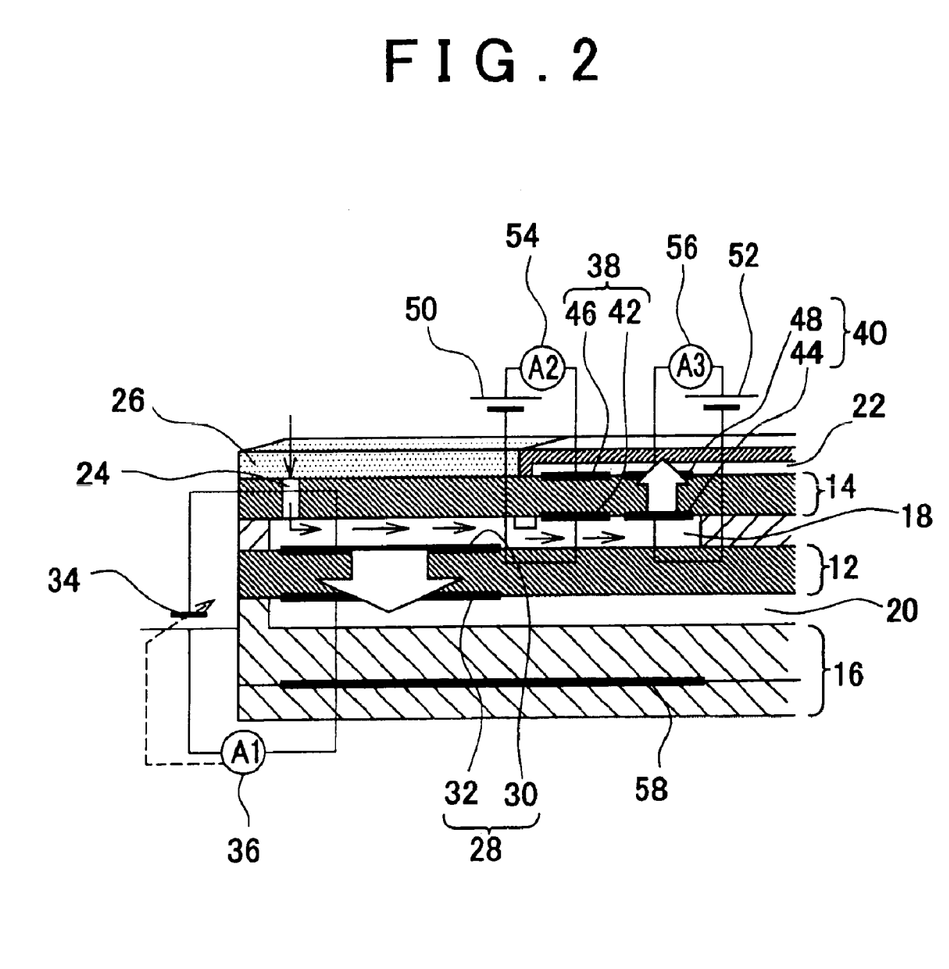
FIG. 2 is a perspective cross-sectional view showing the configuration of the gas concentration detecting apparatus shown in FIG. 1.

FIG. 2 is a perspective cross-sectional view showing the configuration of the gas concentration detecting apparatus 10. As shown in FIG. 2, the gas concentration detecting apparatus 10 includes zirconia layers 12, 14 and an insulation layer 16. A gas detection chamber 18 is provided between two zirconia layers 12, 14. Atmosphere chambers 20, 22 are formed so as to be isolated from the gas detection chamber 18 by the zirconia layers 12, 14 at positions adjacent to the zirconia layers 12, 14.

The gas concentration detecting apparatus 10 includes a diffusion hole 24 leading to the gas detection chamber 18. The diffusion hole 24 is a passage for guiding the exhaust gas from the exhaust passage of the internal combustion engine to the gas detection chamber 18. The exhaust gas can flow from the exhaust passage into the diffusion hole 24 through a diffusion resistance layer 26. The diffusion resistance layer 26 is made of porous material that regulates a speed at which the exhaust gas is diffused. With this configuration, the exhaust gas flowing in the exhaust passage is diffused to a border between the diffusion resistance layer 26 and the zirconia layer 14 at the speed regulated by the diffusion resistance layer 26. Then, the exhaust gas is further diffused toward the inside of the gas detection chamber 18 at a speed regulated due to a squeezing effect of the diffusion hole 24.

The exhaust gas flowing into the gas detection chamber 18 from the diffusion hole 24 flows in the gas detection chamber 18 along a predetermined path. A pump cell 28 is provided in this path. The pump cell 28 is composed of the zirconia layer 12, and a gas-side electrode 30 and an atmosphere-side electrode 32 that are disposed on both sides of the zirconia layer 12. The gas-side electrode 30 has low activity to NOx (for example, a Pt—Au alloy electrode), and is provided so as to be exposed to the gas detection chamber 18. The atmosphere-side electrode 32 is made of Pt, and is provided so as to be exposed to the atmosphere chamber 20.

A variable power source 34 which applies a voltage from the atmosphere-side electrode 32 toward the gas-side electrode 30 is connected to a portion between the gas-side electrode 30 and the atmosphere-side electrode 32. An electric current detector 36 which detects an electric current A1 flowing in the pump cell 28 is connected to the electrodes 30, 32. The variable power source 34 and the electric current detector 36 are included in a control circuit that will be described later.

A monitor cell 38 and a sensor cell 40 are provided downstream of the pump cell 28 so as to be adjacent to each other. In FIG. 2, the monitor cell 38 is positioned upstream of the sensor cell 40 for the sake of convenience. However, in reality, these cells are provided so as to be adjacent to each other in a direction perpendicular to the direction in which the exhaust gas flows.

The monitor cell 38 is composed of the zirconia layer 14, the gas-side electrode 42 that is exposed to the gas detection chamber 18, and the atmosphere-side electrode 46 that is exposed to the atmosphere chamber 22. The sensor cell 40 is composed of the zirconia layer 14, the gas-side electrode 44 that is exposed to the gas detection chamber 18, and the atmosphere-side electrode 48 that is exposed to the atmosphere chamber 22. The gas-side electrode 42 of the monitor cell 38 has low activity to NOx, and is made of Pt—Au alloy or the like. Meanwhile, the gas-side electrode 44 of the sensor cell 40 has high activity to NOx, and is made of Pt—Rh alloy or the like. The atmosphere-side electrodes 46, 48 are made of Pt as well as the pump cell 28.

A constant voltage power source 50 which applies a voltage from the atmosphere-side electrode 46 toward the gas-side electrode 42, and an electric current detector 54 which detects an electric current A2 flowing in the monitor cell 38 are connected to the monitor cell 38. Also, a constant voltage power source 52 which applies voltage from the atmosphere-side electrode 48 toward the gas-side electrode 44, and an electric current detector 56 which detects an electric current A3 flowing in the sensor cell 40 are connected to the sensor cell 40. The constant voltage power sources 50, 52, and the electric current detectors 54, 56 are included in the control circuit that will be described later.

A heater 58 is provided inside the insulation layer 16. The pump cell 28, the monitor 38, and the sensor cell 40 are heated by the heater 58, whereby the temperature of each of the cells is increased to an appropriate activation temperature.

When an appropriate voltage is applied to the pump cell 28 after the temperature of the pump cell 28 has reached the activation temperature, the pump cell 28 decomposes $NO_2$ contained in NOx in the exhaust gas into NO and oxygen such that NOx is converted to single gas NO. Thus, almost all the oxygen existing in the exhaust gas is discharged. In this case, the value of the electric current A1 flowing in the pump cell 28 substantially corresponds to the concentration of oxygen in the exhaust gas flowing into the gas detection chamber 18, that is, an air/fuel ratio A/F of the exhaust gas. Therefore, according to the gas concentration detecting apparatus 10 in the embodiment of the invention, it is possible to detect the air/fuel ratio A/F of the exhaust gas based on the output of the electric current detector 36.

In the gas concentration detecting apparatus 10, the exhaust gas in which there is almost no oxygen and NOx is converted to single gas NO flows in the downstream of the pump cell 28. The monitor cell 38 pumps out oxygen which remains in the exhaust gas after the temperature of the monitor cell 38 has reached the activation temperature, thereby generating the electric current A2 corresponding to the concentration of oxygen in the downstream of the pump cell 28. Therefore, according to the gas concentration detecting apparatus 10 in the embodiment of the invention, it is possible to detect the concentration of the oxygen which remains in the exhaust gas in the downstream of the pump cell 28, based on the output of the electric current detector 54.

The sensor cell 40 decomposes NO in the exhaust gas into nitrogen and oxygen after the temperature of the sensor cell 40 has reached the activation temperature. Further, the sensor cell 40 pumps out all the oxygen which remains in the gas detection chamber 18, thereby generating the electric current A3. Therefore, the value of the electric current A3 corresponds to the sum of the concentration of the oxygen which remains in the exhaust gas in the downstream of the pump cell 28 and the concentration of the oxygen which is generated by decomposing NO. Thus, it is possible to detect the sum of the concentration of the oxygen which remains in the exhaust gas in the downstream of the pump cell 28 and the concentration of the oxygen which is generated by decomposing NO, based on the output of the electric current detector 56.

Further, the value obtained by subtracting the electric current A2 detected by the electric current detector 54 from the electric current A3 detected by the electric current detector 56 corresponds to the concentration of NO existing in the exhaust gas in the downstream of the pump cell 28, that is, the concentration of NOx in the exhaust gas flowing into the gas detection chamber 18. Therefore, according to the gas concentration detecting apparatus in the embodiment of the invention, it is possible to detect the concentration of NOx in the exhaust gas based on the outputs of the two electric current detectors 54, 56.

Referring to FIG. 1 again, the entire configuration of the gas concentration detecting apparatus and the failure diagnostic apparatus for the gas concentration detecting apparatus in the embodiment of the invention will be described. As shown in FIG. 1, a control circuit 60 is connected to the gas concentration detecting apparatus 10. An engine control electronic control unit (hereinafter, referred to as engine control ECU) 70 is connected to the control circuit 60.

Communications are conducted between the control circuit 60 and the ECU 70 using a predetermined protocol. For example, the ECU 70 outputs a request for starting warming-up of the cells (hereinafter, referred to as warming-up start request) toward the control circuit 60 when a predetermined condition for starting warming-up is fulfilled. The control circuit 60 supplies the ECU 70 with outputs indicating the concentration of NOx, the air/fuel ratio A/F, the concentration of oxygen, and the like. In FIG. 1, the control circuit 60 is provided so as to be separate from the ECU 70. However, the control circuit 60 does not necessarily need to be separate from the ECU 70, and may be included in the ECU 70.

The control circuit 60 includes a low electric current output detecting portion which detects the electric current A2 flowing in the monitor cell 38 and the electric current A3 flowing in the sensor cell 40. The aforementioned constant voltage power sources 50, 52, and the electric current detectors 54, 56 are included in the low electric current output detecting portion. That is, the control circuit 60 applies an appropriate voltage to each of the monitor cell 38 and the sensor cell 40 using each of the constant voltage power sources 50, 52 when the gas concentration detecting apparatus 10 needs to be operated. Further, the control circuit 60 detects each of the small electric currents A2, A3 that are generated in the monitor cell 38 and the sensor cell 40 by applying the voltages, using each of the electric current detectors 54, 56.

The control circuit 60 includes an oxygen concentration control portion. The aforementioned variable power source 34 and the electric current detector 36 are included in the oxygen concentration control portion. As described above, the pump cell 28 of the gas concentration detecting apparatus 10 has a function of pumping out oxygen in the exhaust gas flowing into the gas detection chamber 18. It is desirable that the pump cell 28 should discharge as much oxygen as possible without decomposing NO in the exhaust gas in order for the gas concentration detecting apparatus 10 to accurately detect the concentration of NOx in the exhaust gas.

The amount of oxygen discharged by the pump cell 28 is correlated with the voltage applied to the pump cell 28 as long as oxygen remains in the gas detection chamber 18. Therefore, it is necessary to apply, to the pump cell 28, at least a voltage corresponding to the amount of oxygen that needs to be discharged. Meanwhile, the value of the applied voltage should not be unnecessarily high, since NO in the exhaust gas is decomposed when the applied voltage is extremely high. Therefore, the voltage applied to the pump cell 28 needs to be set to an appropriate value corresponding to the concentration of oxygen in the exhaust gas.

The oxygen concentration control portion controls the value of the voltage applied to the pump cell 28 to the appropriate value. More particularly, the variable power source 34 is controlled such that the relation between the electric current A1 and the applied voltage becomes appropriate. In other words, when it is determined that the electric current A1 is extremely large with respect to the applied voltage, the variable power source 34 is controlled such that the applied voltage is increased. Meanwhile, when it is determined that the electric current A1 is extremely small with respect to the applied voltage, the variable power source 34 is controlled such that the applied voltage is decreased. The value of the voltage applied to the pump cell 28 becomes substantially equal to the appropriate value by this control. As a result, almost all the oxygen contained in the exhaust gas is discharged from the gas detection chamber 18 without decomposing NO in the exhaust gas. In this case, the value of the electric current A1 detected by the electric current detector 36 corresponds to the concentration of oxygen in the exhaust gas, that is, the air/fuel ratio A/F of the exhaust gas.

The control circuit 60 includes a heater control portion. As described above, the ECU 70 outputs the warming-up start request toward the control circuit 60 when the predetermined condition for starting warming-up is fulfilled after the internal combustion engine is started. When the heater control portion receives the request, the heater control portion starts to supply power to the heater 58 included in the gas concentration detecting apparatus 10. As a result, the heater 58 generates heat, and each of the pump cell 28, the monitor cell 38, and the sensor cell 40 is increased to the activation temperature.

A diagnostic portion is included in the control circuit 60. The diagnostic portion is a characteristic portion of the failure diagnostic apparatus in the embodiment, and determines whether there is disconnection in the monitor cell 38 or the sensor cell 40.

When there is disconnection in the monitor cell 38 or the sensor cell 40, the value of the electric current A2 flowing in the monitor cell 38 and the value of the electric current A3 flowing in the sensor cell 40 becomes zero, irrespective of the concentration of remaining oxygen or the concentration of NOx. However, the values of the electric currents A2, A3 may become zero even when there is no disconnection. Also, each of the values of the electric currents A2, A3 may instantaneously become a value other than zero due to influence of noise when there is disconnection. Therefore, disconnection cannot be detected simply by monitoring the electric currents A2, A3.

Figure 3A:
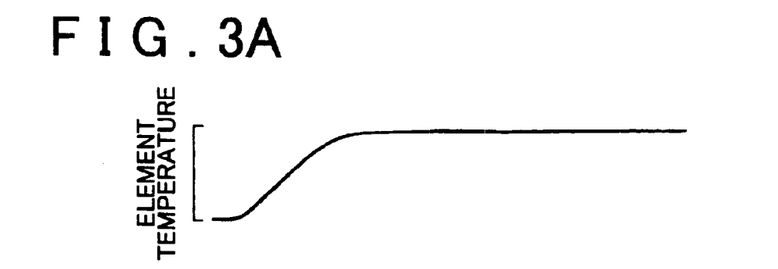
FIG. 3A is a timing chart showing a change in the temperature of an element of the gas concentration detecting apparatus shown in FIG. 1.
Figure 3B:
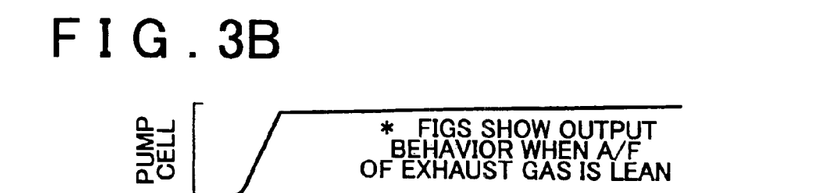
FIG. 3B is a timing chart showing a change in an electric current flowing in a pump cell of the gas concentration detecting apparatus shown in FIG. 1 after a heater starts heating.
Figure 3C:
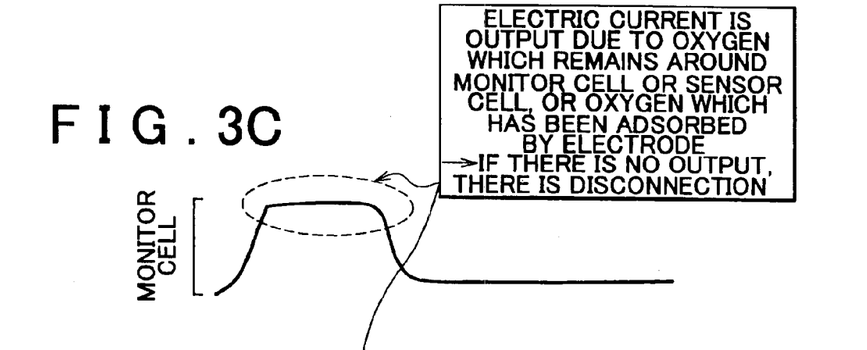
FIG. 3C is a timing chart showing a change in an electric current flowing in a monitor cell of the gas concentration detecting apparatus shown in FIG. 1 after the heater starts heating.
Figure 3D:
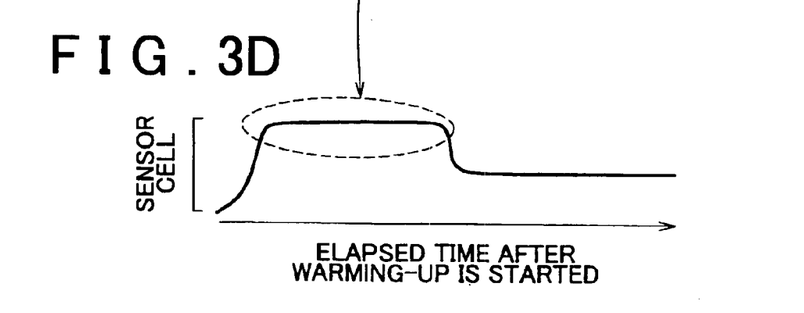
FIG. 3D is a timing chart showing a change in an electric current flowing in a sensor cell of the gas concentration detecting apparatus shown in FIG. 1 after the heater starts heating.

FIGS. 3A to 3D is a timing chart describing a principle for detecting disconnection in the sensor cell 38 or the pump cell 40. More particularly, FIG. 3A shows a change in the temperature of an element in the gas concentration detecting apparatus 10, that is, a change in the temperature of the pump cell 28, the monitor cell 38, and the sensor cell 40, and the like. FIG. 3B, FIG. 3C, and FIG. 3D show a change in the electric current A1 flowing in the pump cell 28, a change in the electric current A2 flowing in the monitor cell 38, and a change in the electric current A3 flowing in the sensor cell 40, respectively.

When the temperature of each of the pump cell 28, the monitor cell 38, and the sensor cell 40 is increased to the activation temperature, each of the cells performs the normal function described above. The waveform of the electric current A1 shown in FIG. 3B is obtained in a case where the air/fuel ratio of the exhaust gas is lean when the heater 58 starts heating. As shown in FIG. 3B, the electric current A1 flowing in the pump cell 28 is increased with an increase in the temperature of the pump cell 28 in the case where the air/fuel ratio of the exhaust gas is lean. However, this waveform of the electric current A1 is obtained only in the case where the air/fuel ratio of the exhaust gas is lean. In the case where the air/fuel ratio of the exhaust gas is stoichiometric, the electric current A1 is maintained at a value in the vicinity of zero irrespective of the increase in the temperature of the pump cell 28. In the case where the air/fuel ratio of the exhaust gas is rich, the value of the electric current A1 becomes a negative value as the temperature of the pump cell 28 is increased.

As shown in FIG. 3C and FIG. 3D, an initial electric current of approximately 3 to 4 $\mu A$ flows in each of the monitor cell 38 and the sensor cell 40 during a certain period while the temperature of each cell is increased, irrespective of the air/fuel ratio of the exhaust gas. It is considered that the initial electric current is generated when the monitor cell 38 or the sensor cell 40 pumps out the oxygen which remains around the cell, or the oxygen which has been adsorbed by the gas-side electrode 42 or the gas-side electrode 44 of the cell as the temperature of the cell is increased.

It is considered that the same phenomenon occurs also in the pump cell 28. However, the electric current A1 which is sufficiently large flows in the pump cell 28 in a normal operational state. Therefore, it is not necessarily easy to determine whether the initial electric current flows in the pump cell 28 as the temperature of the pump cell 28 is increased. Meanwhile, each of the values of the electric currents A2, A3 flowing in the monitor cell 38 and the sensor cell 40 is several tens of nA in the normal operational state, which is a sufficiently small value. Therefore, the value of the aforementioned initial electric current (3 to 4 $\mu A$) is a sufficiently large value in the monitor cell 38 and the sensor cell 40. Thus, it is easy to determine whether the initial electric current flows in the monitor cell 38 or the sensor cell 40 as the temperature of the cell is increased.

In the case where there is disconnection in the monitor cell 38 or the sensor cell 40, the aforementioned initial electric current is not generated while the temperature of the cell is increased. In the case where there is no disconnection in the monitor cell 38 or the sensor cell 40, the initial electric current continues to flow in the cell during a certain period while the temperature of the cell is increased, which is evidently different from the case where there is influence of noise. Therefore, in the failure diagnostic apparatus according to the embodiment of the invention, it is possible to determine whether there is disconnection in the monitor cell 38 or the sensor cell 40, based on whether the electric current A2 or the electric current A3 that is estimated to be the initial electric current continues to flow in the monitor cell 38 or the sensor cell 40 during the certain period after the heater 58 starts heating.

Figure 4A:
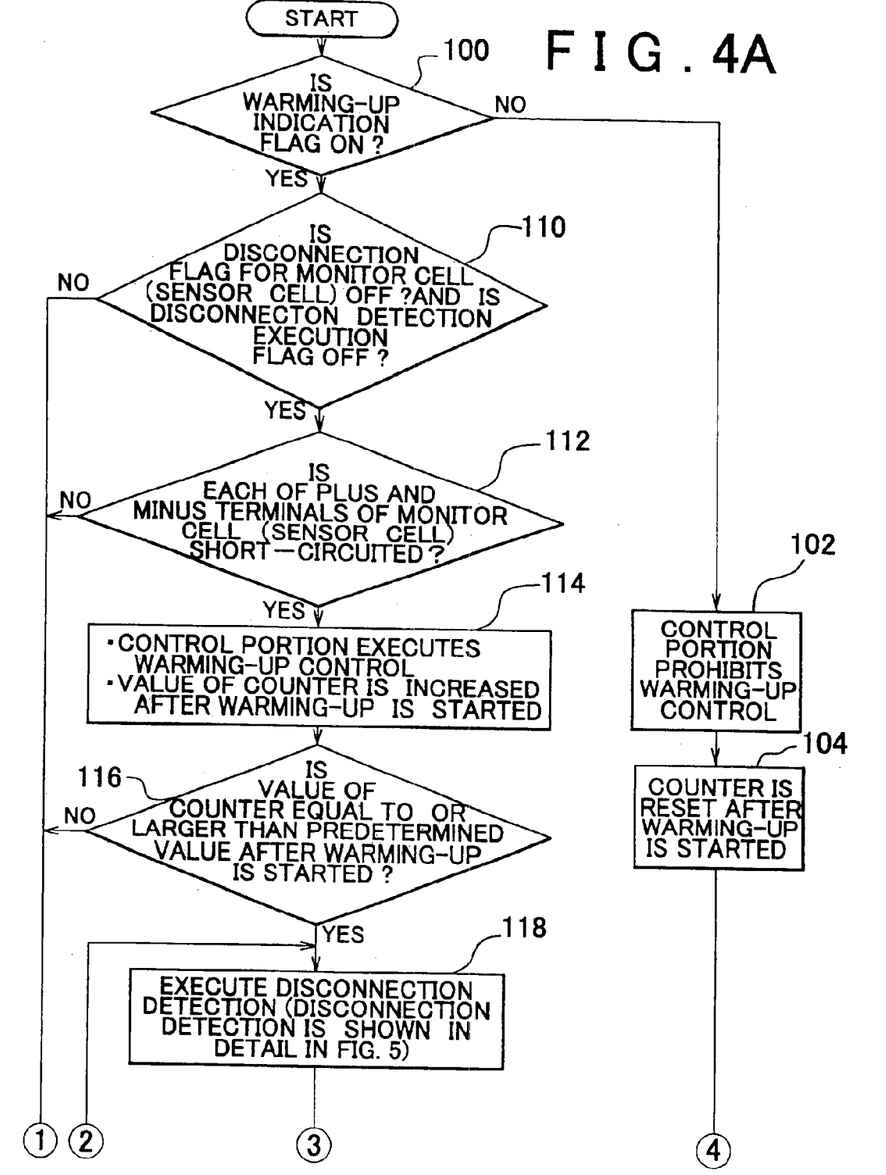
FIG. 4A is a flowchart of a control routine executed by the failure diagnostic apparatus shown in FIG. 1.
Figure 4B:
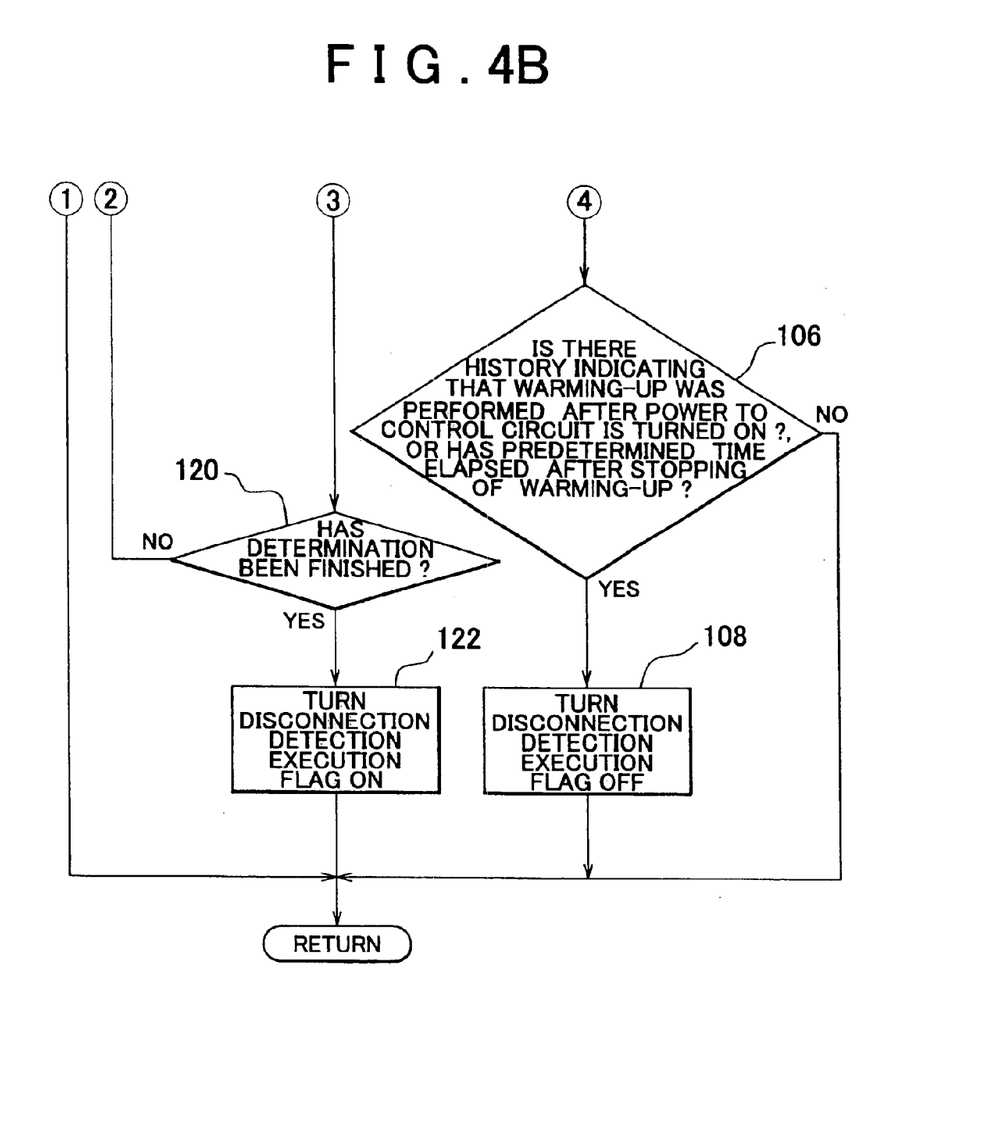
FIG. 4B is a flowchart of a control routine executed by the failure diagnostic apparatus shown in FIG. 1.

FIG. 4A and FIG. 4B is a flowchart of a routine for detecting disconnection in the monitor cell 38 or the sensor cell 40 according to the aforementioned principle, which is executed by the control circuit 60.

In the routine shown in FIG. 4A and FIG. 4B, first, it is determined whether the ECU 70 has output the warming-up start request. More particularly, it is determined whether a warming-up indication flag for indicating whether the request has been output is turned ON (step 100).

As described above, the ECU 70 generates the warming-up start request when the predetermined condition for starting warming-up is fulfilled after the internal combustion engine is started. More particularly, the predetermined condition for starting warming-up is regarded to be fulfilled when a condition for eliminating dew condensation in the exhaust passage is fulfilled. For example, when the internal combustion engine is started while cold, dew condensation is caused in the exhaust passage. Under such circumstances, water drops generated by dew condensation may attach to the gas concentration detecting apparatus 10. In the failure diagnostic apparatus according to the embodiment of the invention, the heater 58 does not perform heating under the circumstances where water drops may attach to the gas concentration detecting apparatus 10, and starts heating when the aforementioned condition for starting warming-up is fulfilled.

When it is determined that the warming-up indication flag is not ON in step 100 in the routine shown in FIG. 4A and FIG. 4B, warming-up of the gas concentration detecting apparatus 10 by the heater 58 is prohibited (step 102).

Subsequently, a counter for measuring an elapsed time after the warming-up of the gas concentration detecting apparatus 10 is started is reset (step 104).

Subsequently, it is determined whether there is a history indicating that the warming-up was performed by the heater 58 after the internal combustion engine was started, that is, the power to the control circuit 60 was turned ON, and if there is the history, it is determined whether the elapsed time after the stopping of the warming-up that was once started has reached the predetermined time (step 106).

As a result, when it is determined that the warming-up was not performed by the heater 58 after the power to the control circuit 60 is turned ON, or when a sufficient time has elapsed after the stopping of the warming-up, it can be determined that the monitor cell 38 and the sensor cell 40 are sufficiently cooled at this time. In this case, a disconnection detection execution flag is turned OFF such that disconnection detection is permitted to be executed (step 108).

Meanwhile, when none of the aforementioned conditions are fulfilled, that is, when there is the history that the warming-up was performed by the heater 58 after the power to the control circuit 60 was turned ON, and the elapsed time after the stopping of the warming-up has not reached the predetermined time, no process is executed, and the present routine is finished. In this case, the disconnection detection execution flag is maintained in the state during the previous process cycle. The disconnection detection execution flag is turned ON when disconnection detection for the monitor cell 38 (or the sensor cell 40) is finished, as described later. According to the aforementioned processes, in a case where the disconnection detection was not finished during the previous process cycle, the present process cycle is finished with the disconnection detection execution flag being OFF as in the case where the condition in step 106 is fulfilled. Meanwhile, in a case where the disconnection detection was finished during the previous process cycle, the present process cycle is finished with the disconnection flag being ON.

When it is determined that the warming-up indication flag is ON in step 100 in the routine shown in FIG. 4A and FIG. 4B, it is determined whether a disconnection flag for the monitor cell 38 (or the sensor cell 40) is OFF, and whether the disconnection detection execution flag for the monitor cell 38 (or the sensor cell 40) is OFF (step 110).

The disconnection flag is turned ON when disconnection in the monitor cell 38 (or the sensor cell 40) is detected, as described later. Accordingly, when the disconnection flag is ON, it can be determined that there is disconnection in the monitor cell 38 (or the sensor cell 40). When it is determined that the disconnection flag is ON, or when it is determined that the disconnection detection execution flag is ON, it is determined that the disconnection detection does not need to be executed, or should not be executed. Thereafter, the present process cycle is finished quickly.

Meanwhile, when it is determined that the disconnection flag is OFF, and the disconnection detection execution flag is also OFF in step 110, a disconnection detection process is executed. More particularly, it is determined whether each of the two electrodes 42, 46 (or each of the two electrodes 44, 48) of the monitor cell 38 (or the sensor cell 40) is short-circuited with the power source or the ground (step 112).

A potential sensor which detects the potentials of the gas-side electrodes 42, 44 and the atmosphere-side electrodes 46, 48 of the monitor cell 38 and the sensor cell 40 is provided in the diagnostic portion of the control circuit 60. In step 112, the potential sensor measures the potential of each electrode, and it is determined whether each electrode is short-circuited with the power source or the ground based on the measured potential of each electrode. When it is detected that at least one of the two electrodes is short-circuited, it is determined that disconnection detection does not need to be executed, and the present process cycle is finished quickly.

When it is determined that neither the gas-side electrode 42 (or the gas-side electrode 44) or the atmosphere-side electrode 46 (or the atmosphere-side electrode 48) is short-circuited, the heater 58 starts the warming-up of the gas concentration detecting apparatus 10. Further, the value of the counter for measuring a time after the warming-up is started is increased (step 114).

Subsequently, it is determined whether the measured value of the counter is equal to or larger than a predetermined determination value (step 116).

The aforementioned determination value is a predetermined value corresponding to the elapsed time after the warming-up is started until the initial electric current shown in FIG. 3C or FIG. 3D starts to flow in each of the monitor cell 38 and the sensor cell 40. Accordingly, when it is determined that the measured value of the counter has not reached the determination value, it can be determined that the initial electric current has not flown in the monitor cell 38 or the sensor cell 40. Meanwhile, when it is determined that the measured value of the counter has reached the determination value, it can be determined that the initial electric current has started to flow in each of the monitor cell 38 and the sensor cell 40.

When it is determined that the measured value of the counter has not reached the determination value in step 116 in the routine shown in FIG. 4A and FIG. 4B, it is determined that the period during which the disconnection detection should be executed has not been reached, and the present process cycle is finished quickly. Meanwhile, when it is determined that the measured value of the counter has reached the determination value, the disconnection detection process is executed (step 118).

Figure 5:
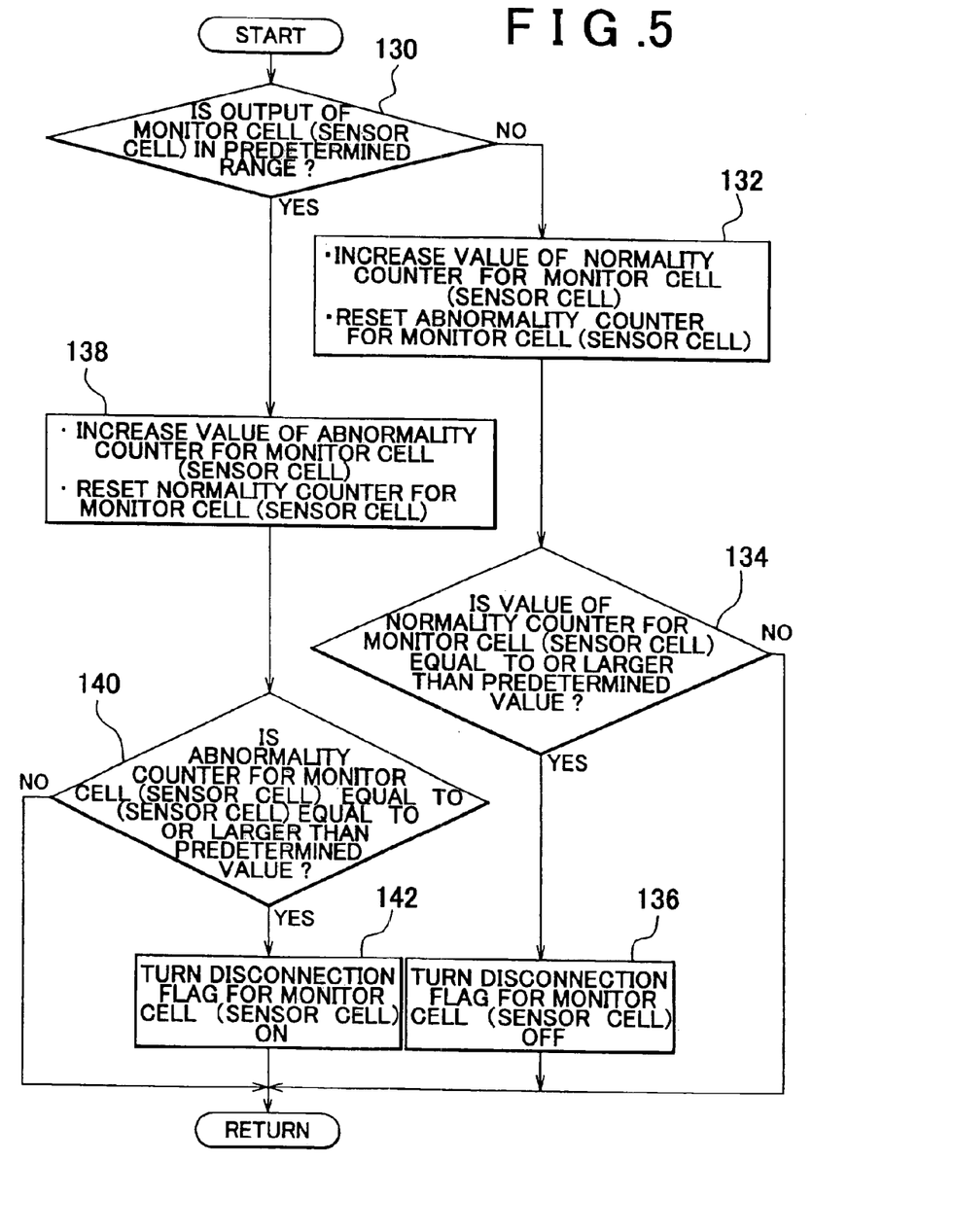
FIG. 5 is a flowchart describing a disconnection detection process executed in step 118 in the flowchart shown in FIG. 4A and FIG. 4B.

FIG. 5 is a flowchart specifically describing the disconnection detection process which is executed in step 118.

It is determined whether the output of the monitor cell 38 (or the sensor cell 40) is in a predetermined range. More particularly, it is determined whether the electric current A2 flowing in the monitor cell 38 (or the electric current A3 flowing in the sensor cell 40) is smaller than a determination value XnA, which is a sufficiently small value as compared with the value of the initial electric current. (step 130).

When the electric current A2 (or the electric current A3) is larger than the determination value XnA, it can be determined that there is a high possibility that the initial electric current appropriately flows in the monitor cell 38 (or the sensor cell 40). In this case, the value of a normality counter for the monitor cell 38 (or the sensor cell 40), which indicates that the cell is normally operated, is increased, and an abnormality counter for the cell, which indicates that there is abnormality in the cell, is reset (step 132).

Next, it is determined whether the measured value of the normality counter for the monitor cell 38 (or the sensor cell 40) is equal to or larger than the predetermined value (step 134).

When the measured value of the normality counter is smaller than the predetermined value, the possibility that the value of the electric current A2 (or the electric current A3) temporarily becomes large due to influence of noise or the like cannot be denied. Therefore, in this case, the present process cycle is finished with the determination concerning disconnection detection being suspended.

Meanwhile, when it is determined that the measured value of the normality counter is equal to or larger than the predetermined value, it can be determined that the electric current A2 (or the electric current A3) is maintained at a large value such that the electric current is regarded as the initial electric current. In this case, in the routine shown in FIG. 5, it is determined that the initial electric current flows in the monitor cell 38 (or the sensor cell 40), and the disconnection flag is turned OFF so as to indicate that there is no disconnection in the monitor cell 38 (or the sensor cell 40) (step 136).

When it is determined that the output of the monitor cell 38 (or the sensor cell 40) is in the predetermined range, that is, it is determined that the electric current A2 (or the electric current A3) is smaller than the determination value XnA in step 130 in the routine shown in FIG. 5, it can be determined that the initial electric current does not flow in the monitor cell 38 (or the sensor cell 40). In this case, the value of the abnormality counter for the monitor cell 38 (or the sensor cell 40) is increased, and the normality counter for the cell is reset (step 138).

Subsequently, it is determined whether the measured value of the abnormality counter for the monitor cell 38 (or the sensor cell 40) is equal to or larger than the predetermined value (step 140).

When the measured value of the abnormality counter is smaller than the predetermined value, the possibility that the electric current A2 (or the electric current A3) temporarily becomes small due to influence of noise or the like cannot be denied. Therefore, in this case, the present process cycle is finished with the determination concerning disconnection detection being suspended.

Meanwhile, when it is determined that the measured value of the abnormality counter is equal to or larger than the predetermined value in step 140, it can be determined that the electric current A2 (or the electric current A3) is maintained at a small value, which is smaller than the value of the initial electric current, over predetermined times. In this case, it is determined that the initial electric current does not flow in the monitor cell 38 (or the sensor cell 40) in the routine shown in FIG. 5. The disconnection flag for the monitor cell 38 (or the sensor cell 40) is turned ON so as to indicate that there is disconnection in the monitor cell 38 (or the sensor cell 40) (step 142).

According to the aforementioned procedure, the disconnection detection process for the monitor cell 38 (or the sensor cell 40) is executed in step 118 shown in FIG. 4A. When the process is finished, it is determined whether the determination concerning disconnection detection has been finished in the routine shown in FIG. 4A and FIG. 4B (step 120).

While it is determined that the determination concerning disconnection detection has not been finished, the process in step 118 is repeated. Meanwhile, when it is determined that the determination concerning disconnection detection has been finished, the disconnection detection execution flag is turned ON, and then the present process cycle is finished (step 122).

As described so far, according to the routine shown in FIG. 4A and FIG. 4B and FIG. 5, whether there is disconnection in the monitor cell 38 or the sensor cell 40 can be determined based on whether the electric current that is regarded as the initial electric current appropriately flows in the cell during a period in which the initial electric current should flow in the cell. Thus, the failure diagnostic apparatus in the embodiment of the invention can accurately and quickly detect disconnection in the monitor cell 38 or the sensor cell 40 included in the gas concentration detecting apparatus 10.

In the aforementioned embodiment, the period during which the disconnection detection should be executed is determined based on the elapsed time after the heater 58 starts warming-up. However, the invention is not limited to the method of determining the period during which the disconnection detection should be executed. In other words, the disconnection detection may be executed during the period in which the initial electric current should flow in each of the monitor cell 38 and the sensor cell 40. For example, a time when the temperature of the cell is increased to a temperature at which the initial current is generated may be detected, and the disconnection detection may be executed at the time. Whether the temperature of the cell is increased to the temperature at which the initial electric current is generated may be determined based on whether the detected alternating current resistance value of one of the pomp cell 28, the monitor cell 38, and the sensor cell 40 is decreased.

In the aforementioned embodiment, the disconnection detection for the monitor cell 38 or the sensor cell 40 is executed by determining whether the appropriate electric current flows in the cell during the period in which the initial electric current should flow in the cell. However, whether there is disconnection can be determined by determining whether the appropriate electric current flows in each cell during a period in which a predetermined electric current should flow in each cell. Accordingly, the invention is not limited to the aforementioned method of determining whether there is disconnection.

That is, whether there is disconnection in the monitor cell 38 or the sensor cell 40 may be determined based on whether the appropriate electric current A2 or the appropriate electric current A3 is generated under the circumstances where a predetermined electric current should flow in the cell (for example, under the circumstances where the air-fuel ratio of the exhaust gas is made lean, and the operation of the pump cell 28 is stopped). Also, disconnection detection may be executed for the pump cell 28. That is, whether there is disconnection in the pump cell 28 may be determined based on whether the appropriate electric current A1 is generated under the circumstances where a predetermined electric current should flow in the pump cell 28 (for example, under the circumstances where the air-fuel ratio of the exhaust gas is fixed to be lean).

In the aforementioned embodiment of the invention, the control circuit 60 executes the process in step 116, whereby "flowing period detector" according to the invention is realized. Also, the control circuit 60 executes the process in steps 138 to 142, whereby "determining device" according to the invention is realized.

In the aforementioned embodiment of the invention, the control circuit 60 measures an elapsed time after the warming-up by the heater 58 is started after step 114, whereby "counter" according to the invention is realized.

In the aforementioned embodiment of the invention, the control circuit 60 detects the alternating current resistance value of one of the pump cell 28, the monitor cell 38, and the sensor cell 40, whereby "resistance detector" according to the invention is realized. Also, the control circuit 60 executes the same process as the process in step 116 based on the alternating current resistance value, whereby "resistance reduction detector" according to the invention is realized.

In the aforementioned embodiment of the invention, the control circuit 60 executes the processes in step 106 and 109, whereby "prohibiting device" according to the invention is realized. Also, in the aforementioned embodiment of the invention, the control circuit 60 executes the process in step 112, whereby "short-circuit detector" according to the invention is realized.

While the invention has been described with reference to exemplary embodiments thereof, it is to be understood that the invention is not limited to the exemplary embodiments or constructions. To the contrary, the invention is intended to cover various modifications and equivalent arrangements. In addition, while the various elements of the exemplary embodiments are shown in various combinations and configurations, which are exemplary, other combinations and configurations, including more, less or only a single element, are also within the spirit and scope of the invention.

What is claimed is:

1. A failure diagnostic apparatus for a gas concentration detecting apparatus, comprising:

a heater which heats, to an activation temperature, a cell of the gas concentration detecting apparatus which pumps out oxygen in subject gas, thereby generating an electric current corresponding to a concentration of oxygen in the subject gas;

a flowing period detector which detects a period during which a predetermined electric current should flow in the cell after the heater starts heating; and a determining device which determines that there is disconnection in the cell when the electric current flowing in the cell is smaller than the predetermined electric current during the period in which the predetermined electric current should flow in the cell.

2. The failure diagnostic apparatus according to claim 1, wherein the predetermined electric current is an initial electric current that is generated due to warming-up of the cell.

3. The failure diagnostic apparatus according to claim 2, wherein the gas concentration detecting apparatus includes a pump cell which pumps out, from a detection portion, oxygen contained in the subject gas flowing into the detection portion; and a sensor cell which decomposes NOx contained in the subject gas into nitrogen and oxygen after the pump cell pumps out oxygen, and further pumps out oxygen in the subject gas after decomposing of NOx contained in the subject gas into nitrogen and oxygen, and the cell determined the disconnection by the determining device is the sensor cell.

4. The failure diagnostic apparatus according to claim 2, wherein the gas concentration detecting apparatus includes a pump cell which pumps out, from a detection portion, oxygen contained in the subject gas flowing into the detection portion; a sensor cell which decomposes NOx contained in the subject gas into nitrogen and oxygen after the pump cell pumps out oxygen, and further pumps out oxygen in the subject gas after decomposing of NOx contained in the subject gas into nitrogen and oxygen; and a monitor cell which pumps out oxygen contained in the subject gas after the pump cell pumps out oxygen, and the cell determined the disconnection by the determining device is the monitor cell.

5. The failure diagnostic apparatus according to claim 2, wherein the flowing period detector includes a counter which measures a time until a predetermined time elapses so that at least the beginning of a period during which the initial electric current should flow in the cell is reached after the heater starts heating.

6. The failure diagnostic apparatus according to claim 2, wherein the flowing period detector includes a resistance detector which detects an alternating current resistance value of the cell; and a resistance reduction detector which detects a reduction of the alternating current resistance value to a predetermined resistance value at which the initial electric current is generated.

7. The failure diagnostic apparatus according to claim 1, further comprising a prohibiting device which prohibits a determination on whether there is disconnection in the cell in a case where it is estimated that a temperature of the cell has already become high when the heater starts heating.

8. The failure diagnostic apparatus according to claim 1, wherein the cell includes a gas-side electrode which contacts the subject gas and an atmosphere-side electrode which contacts atmosphere; and the determining device includes a short-circuit detector which detects whether each of the gas-side electrode and the atmosphere-side electrode is short-circuited with a power source or a ground and determines whether there is disconnection in the cell is made only when neither the gas-side electrode or the atmosphere-side electrode is short-circuited with the power source or the ground.

9. A failure diagnostic method for a gas concentration detecting apparatus comprising the steps of:

heating, to an activation temperature, a cell of the gas concentration detecting apparatus which pumps out oxygen in subject gas, thereby generating an electric current corresponding to a concentration of oxygen in the subject gas;

detecting a period during which a predetermined electric current should flow in the cell after heating is started; and determining that there is disconnection in the cell when the electric current flowing in the cell is smaller than the predetermined electric current during the period in which the predetermined electric current should flow in the cell.

10. The failure diagnostic method according to claim 9, wherein the predetermined electric current is an initial electric current which is generated due to warming-up of the cell.

11. The failure diagnostic method according to claim 10, wherein the gas concentration detecting apparatus includes a pump cell which pumps out, from a detection portion, oxygen contained in the subject gas flowing into the detection portion; and a sensor cell which decomposes NOx contained in the subject gas into nitrogen and oxygen after the pump cell pumps out oxygen, and further pumps out oxygen in the subject gas after decomposing of NOx contained in the subject gas into nitrogen and oxygen, and the cell determined the disconnection is the sensor cell.

12. The failure diagnostic method according to claim 10, wherein the gas concentration detecting apparatus includes a pump cell which pumps out, from a detection portion, oxygen contained in the subject gas flowing into the detection portion; a sensor cell which decomposes NOx contained in the subject gas into nitrogen and oxygen after the pump cell pumps out oxygen, and further pumps out oxygen in the subject gas after decomposing of NOx contained in the subject gas into nitrogen and oxygen; and a monitor cell which pumps out oxygen contained in the subject gas after the pump cell pumps out oxygen, and the cell determined the disconnection is the monitor cell.

13. The failure diagnostic method according to claim 10, wherein a time is measuring until a predetermined time elapses so that at least the beginning of a period during which the initial electric current should flow in the cell is reached after the heater starts heating when the period during which the predetermined electric current should flow in the cell is detected.

14. The failure diagnostic method according to claim 10, wherein an alternating current resistance value of the cell is detected; and a reduction of the alternating current resistance value to a predetermined resistance value at which the initial electric current is generated is detected when the period during which the predetermined electric current should flow in the cell is detected.

15. The failure diagnostic method according to claim 9, wherein a determination whether there is on disconnection in the cell is prohibited in a case where it is estimated that a temperature of the cell has already become high when the heater starts heating.

16. The failure diagnostic method according to claim 9, wherein the cell includes a gas-side electrode which contacts the subject gas and an atmosphere-side electrode which contacts atmosphere; it is detected whether each of the gas-side electrode and the atmosphere-side electrode is short-circuited with a power source or a ground when a determination on whether there is disconnection in the cell is made; and the determination on whether there is disconnection in the cell is made only when neither the gas-side electrode or the atmosphere-side electrode is short-circuited with the power source or the ground.

* * * * *